United States Patent
Qiu et al.

(10) Patent No.: US 10,197,438 B2
(45) Date of Patent: Feb. 5, 2019

(54) DEVICE AND METHOD FOR TESTING IMPEDANCE CHARACTERISTIC AND EXPANSION PERFORMANCE OF SOUND ABSORPTION MATERIAL

(71) Applicant: Goertek Inc., Weifang (CN)

(72) Inventors: Dong Qiu, Weifang (CN); Xiaodong Cao, Weifang (CN)

(73) Assignee: Goertek Inc., Weifang (CN)

( * ) Notice: Subject to any disclaimer, the term of this patent is extended or adjusted under 35 U.S.C. 154(b) by 0 days.

(21) Appl. No.: 15/513,942

(22) PCT Filed: Jun. 15, 2015

(86) PCT No.: PCT/CN2015/081440
§ 371 (c)(1),
(2) Date: Mar. 23, 2017

(87) PCT Pub. No.: WO2016/082526
PCT Pub. Date: Jun. 2, 2016

(65) Prior Publication Data
US 2017/0276540 A1    Sep. 28, 2017

(30) Foreign Application Priority Data

Nov. 28, 2014    (CN) .......................... 2014 1 0713191

(51) Int. Cl.
*G01H 15/00*      (2006.01)
*G10K 11/162*    (2006.01)
(Continued)

(52) U.S. Cl.
CPC ............. *G01H 15/00* (2013.01); *G01B 17/00* (2013.01); *G01H 3/00* (2013.01); *G01N 29/09* (2013.01);
(Continued)

(58) Field of Classification Search
CPC ...... G10H 15/00; G01N 29/032; G01N 29/09; G01N 29/11; G01N 29/223; G01N 29/12; G01N 2291/018; G10K 11/162
(Continued)

(56) References Cited

U.S. PATENT DOCUMENTS 5,792,955 A    8/1998   Song et al.
6,119,521 A    9/2000   Shivashankara et al.
(Continued)

FOREIGN PATENT DOCUMENTS

CN    101696955 A    4/2010
CN    102375031 A    3/2012
(Continued)

OTHER PUBLICATIONS

International Bureau of WIPO, International Search Report and Written Opinion in Application No. PCT/CN2015/080323, dated Nov. 11, 2015.
(Continued)

*Primary Examiner* — Daniel S Larkin
*Assistant Examiner* — Anthony W Megna Fuentes
(74) *Attorney, Agent, or Firm* — LKGlobal | Lorenz & Kopf, LLP

(57) ABSTRACT

Disclosed are a device and a method for testing impedance characteristic and expansion performance of a sound absorption material. The device includes a first cavity and a second cavity which are both sealed. The first cavity is communicated with the second cavity through a slit channel. The second cavity is used for placing a sound absorption material therein. The device further includes a sound excitation source whose sounding face is located in the first cavity and used to provide a testing sound pressure. The device further includes two sound pickup sensors whose sound pickup surfaces are respectively arranged in the first cavity and the
(Continued)

second cavity and respectively used to detect sound pressure in the first cavity and the second cavity. The device further includes a material for enclosing the first cavity and the second cavity is a hard sound insulation material.

6 Claims, 1 Drawing Sheet

(51) Int. Cl.
    *G10H 3/00*     (2006.01)
    *G01N 29/09*     (2006.01)
    *G01B 17/00*     (2006.01)
    *G01H 3/00*     (2006.01)

(52) U.S. Cl.
    CPC ...... *G10K 11/162* (2013.01); *G01N 2291/028* (2013.01)

(58) Field of Classification Search
    USPC ............ 73/574, 589, 645, 865.6, 866, 432.1
    See application file for complete search history.

(56) References Cited

U.S. PATENT DOCUMENTS

| | | | | |
|---|---|---|---|---|
| 9,084,060 | B2* | 7/2015 | Liu | H04R 29/00 |
| 2011/0192231 | A1* | 8/2011 | Dalmont | G01H 15/00 |
| | | | | 73/589 |

FOREIGN PATENT DOCUMENTS

| | | |
|---|---|---|
| CN | 104034808 A | 9/2014 |
| CN | 203929717 U | 11/2014 |
| CN | 104407056 A | 3/2015 |
| JP | 2000121427 A | 4/2000 |
| SU | 1682908 A1 | 10/1991 |

OTHER PUBLICATIONS

State Intellectual Office of The Peoples Republic of China, First Office Action in Application No. 201410713191.6, dated Jul. 6, 2016.

State Intellectual Office of The Peoples Republic of China, Second Office Action in Application No. 201410713191.6, dated Feb. 22, 2017.

* cited by examiner

DEVICE AND METHOD FOR TESTING IMPEDANCE CHARACTERISTIC AND EXPANSION PERFORMANCE OF SOUND ABSORPTION MATERIAL

CROSS-REFERENCE TO RELATED APPLICATIONS

This application is a U.S. National-Stage entry under 35 U.S.C. § 371 based on International Application No. PCT/CN2015/081440 filed Jun. 15, 2015, and which claims priority to Chinese Application No. 201410713191.6, filed Nov. 28, 2014, which are all incorporated herein in their entirety by reference.

TECHNICAL FIELD

This application pertains to the technical field of material performance detection, and particularly to a device and a method for testing impedance characteristic and expansion performance of a sound absorption material.

BACKGROUND

A sound absorption material is a material having a strong performance of absorbing acoustic energy and reducing noise. When the sound absorption material is placed in a cavity, and a cavity is filled with sound pressure, the sound absorption material placed in the cavity absorbs partial acoustic energy, and this is equivalent to expanding a capacity of the cavity. Since the sound absorption material has such expansion characteristic, technician in the acoustic field place the sound absorption material in the cavities of some acoustic products to expand the capacity of the cavities of products without increasing external volume of the products, to improve the performance of acoustic products.

There are many kinds of materials capable of absorbing sound, but not every kind of sound absorption material has a very good expansion performance. To this end, technicians selects and uses a sound absorption material adapted for technical requirements of acoustic products from diverse sound absorption materials. However, currently there is not a device and a method for testing impedance characteristic and expansion performance of a sound absorption material. Technicians can only install each kind of sound absorption material into the acoustic product, then test to see whether the performance of the acoustic product changes or not, and thereby judge which sound absorption material is most adapted for the acoustic product. Such method of testing the sound absorption material is rather backward, causes large waste of manpower and material resources to enterprises, prolongs a development cycle of products, and thereby increases production costs of products.

In addition, other objects, desirable features and characteristics will become apparent from the subsequent summary and detailed description, and the appended claims, taken in conjunction with the accompanying drawings and this background.

SUMMARY

In view of the above drawbacks, the first technical problem to be solved by the present application is to provide a device for testing impedance characteristic and expansion performance of a sound absorption material. The device can test the impedance characteristic and expansion performance of the sound absorption material before it is installed in the acoustic product, thereby providing accurate technical indices for selection of the sound absorption material, eliminating waste of manpower and material resources, shortening the development cycle of acoustic products, and reducing the production costs of the product.

Based on a single general inventive concept, the second technical problem to be solved by the present application is to provide a method for testing impedance characteristic and expansion performance of a sound absorption material. By the method, the impedance characteristic and expansion performance of the sound absorption material can be accurately tested.

To solve the above first technical problem, the present application employs the following technical solutions:

A device for testing impedance characteristic and expansion performance of a sound absorption material comprises: a first cavity and a second cavity which are both sealed, the first cavity being communicated with the second cavity through a slit channel, wherein the second cavity is used for placing a sound absorption material therein; a sound excitation source whose sounding face is located in the first cavity and used to provide a testing sound pressure; two sound pickup sensors whose sound pickup surfaces are respectively arranged in the first cavity and the second cavity and which are respectively used to detect sound pressure in the first cavity and the second cavity; and a material for enclosing the first cavity and the second cavity is a hard sound insulation material.

Preferably, the first cavity and the second cavity each are a cavity with a regular shape.

Preferably, the sounding face of the sound excitation source flushes with a surface of an inner wall of the first cavity.

Preferably, the sound excitation source is a speaker.

Preferably, the sound pickup sensor is a microphone.

Preferably, the sound isolation material is one of metal, bakelite and acrylic.

To solve the above second technical problem, the present application employs the following technical solutions:

A method for testing impedance characteristic and expansion performance of a sound absorption material comprises the following steps:

S1: adjusting a voltage of the sound excitation source to enable the sound pressure in the second cavity to satisfy a sound pressure level needed by the test;

S2: Measuring a sound pressure $P_{11(\omega)}$ in the first cavity via the first sound pickup sensor, and measuring a sound pressure $P_{21(\omega)}$ in the second cavity via the second sound pickup sensor; solving an equivalent acoustic capacitance $C_{a2}$ and an acoustic impedance $Z_{a2(\omega)}$ of the second cavity according to formula $$C_{a2} = \frac{V_2}{\rho C_0^2} \text{ and } Z_{a2(\omega)} = \frac{1}{\omega C_{a2}},$$

wherein $V_2$ is a volume of the second cavity, $\rho$ is air density, $C_0$ is a sound speed, and $\omega$ is an angular speed;

S3: obtaining formula $$Z_{ref(\omega)} = \frac{P_{11(\omega)} - P_{21(\omega)}}{P_{21(\omega)} \times \omega C_{a2}}$$

according to an acoustic circuit that is equivalent to the device when the sound absorption material is not placed in the device, and putting the equivalent acoustic capacitance $C_{a2}$ solved from step S2 into the formula to solve the acoustic impedance $Z_{ref(\omega)}$ of the slit channel;

S4: placing the sound absorption material to be tested in the second cavity, measuring a sound pressure $P_{12(\omega)}$ in the first cavity via the first sound pickup sensor, measuring a sound pressure $P_{22(\omega)}$ in the second cavity via the second sound pickup sensor, obtaining formula $$Z_{L(\omega)} = \frac{P_{22(\omega)}}{\frac{P_{12(\omega)} - P_{22(\omega)}}{Z_{ref(\omega)}}}$$

according to the acoustic circuit that is equivalent to the device after the sound absorption material is placed in the device, putting the acoustic impedance $Z_{ref(\omega)}$ of the slit channel solved in step S3 into the formula to solve a uniform acoustic impedance $Z_{L\ (\omega)}$ after the sound absorption material is placed in the second cavity;

S5: obtaining formula $$Z_{L(\omega)} = \frac{\frac{1}{\omega C_{a2}} \times \frac{1}{\omega C_{dut}}}{\frac{1}{\omega C_{a2}} + \frac{1}{\omega C_{dut}}}$$

according to the acoustic circuit that is equivalent to the device after the sound absorption material is placed in the device, and solving an equivalent acoustic capacitance $C_{dut}$ of the sound absorption material; solving a capacity expansion amount $V_{dut}$ of the sound absorption material according to the formula $V_{dut} = \rho C_0^2 C_{dut}$, and thereby judging the impedance characteristic and expansion performance of the sound absorption material.

Wherein, a sound pressure level needed by the test in step S1 is a sound pressure level of an actual working environment of the sound absorption material.

The present application achieves the following advantageous effects after employing the above technical solutions:

In the present application, the device for testing impedance characteristic and expansion performance of the sound absorption material device comprises: a first cavity and a second cavity which are both sealed, the first cavity being communicated with the second cavity through a slit channel; a sound excitation source whose sounding face is located in the first cavity; two sound pickup sensors respectively used to detect sound pressure in the first cavity and the second cavity; and a material for enclosing the first cavity and the second cavity is a sound insulation material. When the performance of the sound absorption material is tested, the sound pressure in the first cavity and second cavity and the impedance of the slit channel are detected first, then the sound absorption material to be tested is placed in the second cavity, then the sound pressure in the first cavity and second cavity at this time is detected, then the equivalent acoustic capacitance and capacity expansion amount of the sound absorption material are solved from a formula which is obtained from an acoustic circuit equivalently worked out by the device at this time. Whether the sound absorption material satisfies technical requirements of the acoustic product may be judged according to the obtained equivalent acoustic capacitance and capacity expansion amount of the sound absorption material. Hence, the sound absorption material adapted for the acoustic product may be selected in a way that the sound absorption material needn't be installed in the acoustic product. This eliminates waste of manpower and material resources caused by test of sound absorption material for each acoustic product, substantially shortens the time for selecting the sound absorption material, thereby shortening a development cycle of a new product, reducing production costs of products and bringing about larger economic benefits to enterprises.

To conclude, the device and method for testing impedance characteristic and expansion performance of a sound absorption material according to the present application solve the technical problem in the prior art about difficulty in selecting the sound absorption material. The device and method for testing impedance characteristic and expansion performance of the sound absorption material according to the present application implement performance test of the sound absorption material, provide technical indices for selection of the sound absorption material, reduce the production costs of the acoustic product, and bring about larger economic benefits to the enterprises.

The above depictions are only generalization of technical solutions of the present application, which may be implemented according to content of the description to make technical means of the present application clearer. Specific embodiments of the present application are presented below to make the above and other objects, features and advantages of the present application more apparent.

BRIEF DESCRIPTION OF THE DRAWINGS

The present invention will hereinafter be described in conjunction with the following drawing figures, wherein like numerals denote like elements, and.

In the figures, the reference number 10 denotes first cavity, 20 denotes second cavity, 30 denotes slit channel, 40 denotes sound absorption material, 50 denotes sound excitation source, 60 denotes first sound pickup sensor, 62 denotes second sound pickup sensor, $P_{11}$, $P_{21}$ denote sound pressure of the first cavity, $P_{12}$, $P_{22}$ denote sound pressure of the second cavity, $M_a$ denotes sound quality of the slit channel, $R_a$ denotes acoustic impedance of the slit channel, $C_{a1}$ denotes equivalent acoustic capacitance of the first cavity, $C_{a2}$ denotes equivalent acoustic capacitance of the second cavity, $C_{dut}$ denotes equivalent acoustic capacitance of the sound absorption material.

DETAILED DESCRIPTION

The following detailed description is merely exemplary in nature and is not intended to limit the invention or the application and uses of the invention. Furthermore, there is no intention to be bound by any theory presented in the preceding background of the invention or the following detailed description.

The present application will be further illustrated with reference to figures and embodiments.

Figure 1:
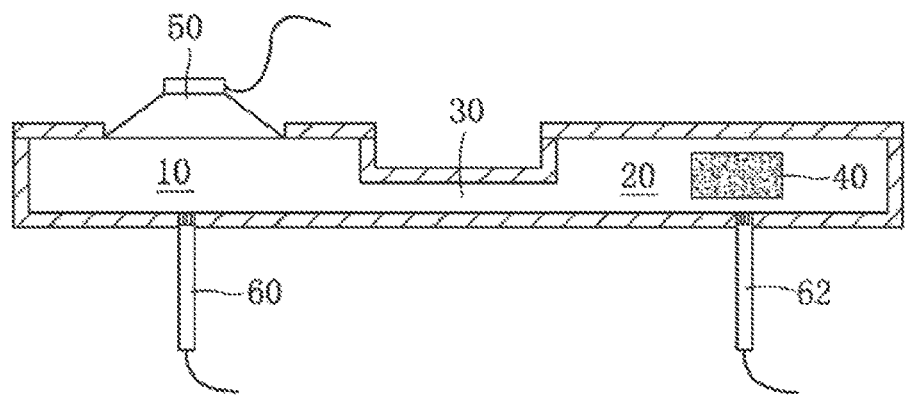
FIG. 1 is a structural schematic view of a device for testing impedance characteristic and expansion performance of a sound absorption material according to the present application.

As shown in FIG. 1, a device for testing impedance characteristic and expansion performance of a sound absorption material comprises: a first cavity 10 and a second cavity 20 which are both sealed, wherein the first cavity 10 is communicated with the second cavity 20 through a slit channel 30. The device further comprises a sound excitation source 50 whose sounding face is located in the first cavity 10, and a first sound pickup sensor 60 whose sound pickup surface is located in the first cavity 10 and a second sound pickup sensor 62 whose sound pickup surface is located in the second cavity 20.

As shown in FIG. 1, both the first cavity 10 and second cavity 20 are a cavity of a regular shape such as cube, cuboid, cylinder or the like. Panel materials enclosing the first cavity 10 and second cavity 20 all are hard sound-isolating materials with strong reflectivity, for example, metallic, bakelite or acrylic plates with a thickness of over 2 mm.

As shown in FIG. 1, in the present embodiment a speaker is selected as the sound excitation source 50 to provide sound pressure upon testing the sound absorption performance. A sounding face of the sound excitation source 50 flushes with the surface of the inner wall of the first cavity so that the sound pressure at all positions in the cavity is in equilibrium.

As shown in FIG. 1, in the present embodiment two high-sound pressure microphones are selected as the first sound pickup sensor 60 and the second sound pickup sensor 62 which are respectively used to detect the sound pressure in the first cavity 10 and the second cavity 20.

Figure 2:
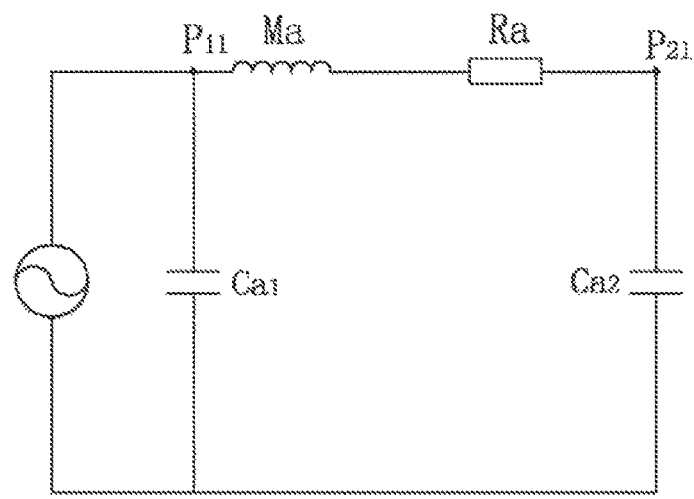
FIG. 2 is an equivalent acoustic circuit diagram when the sound absorption material is not placed in the device for testing impedance characteristic and expansion performance of the sound absorption material according to the present application.

As jointly shown in FIG. 1 and FIG. 2, FIG. 2 is an equivalent acoustic circuit diagram when the sound absorption material is not placed in the device. The acoustic impedance $$Z_{a2(\omega)} = \frac{1}{\omega C_{a2}}$$

of the second cavity 20 is solved from a capacitive reactance formula $$X_C = \frac{1}{\omega C},$$

Wherein, ω is an angular speed, $C_a$ is an equivalent acoustic capacitance of the second cavity 20.

The acoustic impedance $Z_{ref(\omega)}$ of the slit channel 30 may be solved from FIG. 2, $$Z_{ref(\omega)} = \omega M_a + R_a \qquad \text{formula (1)}$$
$$= \frac{P_{11} - P_{21}}{\frac{P_{21}}{Z_{a2}}}$$
$$= \frac{P_{11} - P_{21}}{P_{21} \times \omega C_{a2}}.$$

Figure 3:
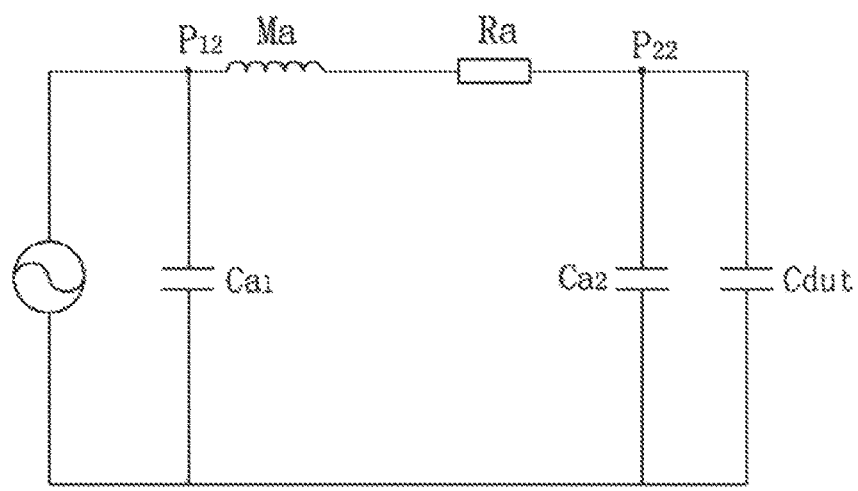
FIG. 3 is an equivalent acoustic circuit diagram after the sound absorption material is placed in the device for testing impedance characteristic and expansion performance of the sound absorption material according to the present application.

As jointly shown in FIG. 1 and FIG. 3, when the performance of the sound absorption material is tested, the sound absorption material 40 is placed in the second cavity 20, whereupon the acoustic circuit that is equivalent to the device after the sound absorption material is placed in the device is as shown in FIG. 3. A uniform acoustic impedance $Z_{L(\omega)}$ after the sound absorption material 40 is placed in the second cavity 20 may be solved according to the acoustic circuit diagram, The acoustic impedance of the sound absorption material 40 is $$Z_{dut} = \frac{1}{\omega C_{dut}}, \qquad \text{formula (2)}$$

$$Z_{L(\omega)} = \frac{Z_{a2} \times Z_{dut}}{Z_{a2} + Z_{dut}}$$
$$= \frac{\frac{1}{\omega C_{a2}} \times \frac{1}{\omega C_{dut}}}{\frac{1}{\omega C_{a2}} + \frac{1}{\omega C_{dut}}}$$

$$Z_{L(\omega)} = \frac{P_{22(\omega)}}{\frac{P_{12(\omega)} - P_{22(\omega)}}{Z_{ref(\omega)}}}, \qquad \text{formula (3)}$$

As shown in FIG. 1, FIG. 2 and FIG. 3, the method of using the above testing device to test impedance characteristic and expansion performance of a sound absorption material comprises the following steps:

S1: calibrating the sound pressure in the second cavity 20, namely, detecting the sound pressure in the second cavity 20 via the second sound pickup sensor 62 by adjusting a voltage of the sound excitation source 50, so that the sound pressure in the second cavity 20 reaches a sound pressure level needed by the test. The sound pressure level needed by the test is consistent with the sound pressure level in the cavity of the acoustic product in which the sound absorption material is to be installed, namely, a sound pressure level of a working environment where the sound absorption material lies when the sound absorption material works.

S2: according to formula $$C_{a2} = \frac{V_2}{\rho C_0^2},$$

calculating an equivalent acoustic capacitance $C_{a2}$ of the second cavity 20 and a corresponding acoustic impedance $$Z_{a2(\omega)} = \frac{1}{\omega C_{a2}}$$

at a
different frequency, wherein:
$V_2$ is a volume of the second cavity 20,
ρ is air density,
$C_0$ is sound speed.

Measuring a sound pressure $P_{11(\omega)}$ in the first cavity 10 at this time via the first sound pickup sensor 60, and measuring a sound pressure $P_{21(\omega)}$ in the second cavity 20 at this time via the second sound pickup sensor 62.

S3: putting the equivalent acoustic capacitance $C_{a2}$ of the second cavity 20, the sound pressure $P_{11(\omega)}$ in the first cavity 10, and the sound pressure $P_{21(\omega)}$ in the second cavity 20 solved in the step S2 into formula (1) to solve the acoustic impedance $Z_{ref(\omega)}$ of the slit channel 30.

S4: placing the sound absorption material 40 to be tested in the second cavity 20, measuring a sound pressure $P_{12(\omega)}$ in the first cavity 10 at this time via the first sound pickup sensor 60, measuring a sound pressure $P_{22(\omega)}$ in the second cavity 20 at this time via the second sound pickup sensor 62, then putting $Z_{ref(\omega)}$ solved in step S3 into formula (3) to solve a uniform acoustic impedance $Z_{L\ (\omega)}$ after the sound absorption material 40 is placed in the second cavity 20.

S5: putting $Z_{L\ (\omega)}$ solved in step S4 into formula (2) to solve an equivalent acoustic capacitance $C_{dut}$ of the sound absorption material 40, $$Z_{L(\omega)} = \frac{\frac{1}{\omega C_{a2}} \times \frac{1}{\omega C_{dut}}}{\frac{1}{\omega C_{a2}} + \frac{1}{\omega C_{dut}}} \quad \text{formula (2)}$$

$$= \frac{1}{\omega C_{dut} + \omega C_{a2}}$$

The following is solved:

$$C_{dut} = \frac{1 - \omega C_{a2} \cdot Z_{L(\omega)}}{\omega Z_{L(\omega)}}$$

$$= \frac{1}{\omega Z_{L(\omega)}} - C_{a2}$$

Putting the solved $C_{dut}$ into formula $V_{dut} = \rho C_0^2 C_{dut}$ to solve a capacity expansion amount $V_{dut}$ of the sound absorption material 40, $$V_{dut} = \rho C_0^2 \left( \frac{1}{\omega Z_{L(\omega)}} - C_{a2} \right),$$

It is feasible to, according to the solved equivalent acoustic capacitance $C_{dut}$ and capacity expansion amount $V_{dut}$ of the sound absorption material 40, determine the impedance characteristic and expansion performance of the sound absorption material 40, and thereby judging whether the tested sound absorption material 40 satisfies technical requirements of the acoustic product.

As known from the above, the device and method for testing impedance characteristic and expansion performance of a sound absorption material according to the present application solve the technical difficulty of failure to test the impedance characteristic and expansion performance of the sound absorption material. With the device and method of the present application, it is unnecessary to install the sound absorption material in the acoustic product to test whether the performance of the acoustic product is improved to judge whether the sound absorption material meets technical requirements of the acoustic product when the sound absorption material is selected for the acoustic product. Technicians may select a suitable sound absorption material for the acoustic product very quickly only according to the measured parameters of the sound absorption material such as equivalent acoustic capacitance and capacity expansion amount, thereby substantially shortening the development cycle of a new product, and meanwhile eliminating large waste of manpower and material resources, greatly reducing production costs of the acoustic product and bringing about larger economic benefits to the enterprises.

Technical terms (e.g., the first cavity and the second cavity) denoted by a serial number involved in the description are only intended to distinguish technical features, and does not represent positional relationship, assembling order, and operation order of the technical features.

The present application is not limited to the above specific embodiments. Diverse variations made by those having ordinary skill in the art starting from the above concept without making any inventive efforts all fall within the protection scope of the present application.

While at least one exemplary embodiment has been presented in the foregoing detailed description, it should be appreciated that a vast number of variations exist. It should also be appreciated that the exemplary embodiment or exemplary embodiments are only examples, and are not intended to limit the scope, applicability, or configuration of the invention in any way. Rather, the foregoing detailed description will provide those skilled in the art with a convenient road map for implementing an exemplary embodiment, it being understood that various changes may be made in the function and arrangement of elements described in an exemplary embodiment without departing from the scope of the invention as set forth in the appended claims and their legal equivalents.

The invention claimed is:

1. A method for testing impedance characteristic and expansion performance of a sound absorption material by using a testing device, wherein the testing device comprises:
   a first cavity and a second cavity which are both sealed, the first cavity being communicated with the second cavity through a slit channel, wherein the second cavity is used for placing a sound absorption material therein;
   a sound excitation source whose sounding face is located in the first cavity and used to provide a testing sound pressure; and
   two sound pickup sensors whose sound pickup surfaces are respectively arranged in the first cavity and the second cavity and which are respectively used to detect sound pressure in the first cavity and the second cavity;
   a material for enclosing the first cavity and the second cavity is a sound insulation material,
   wherein the method comprises the following steps:
   S1: adjusting a voltage of the sound excitation source to enable the sound pressure in the second cavity to satisfy a sound pressure level needed by the test;
   S2: measuring a sound pressure $P_{11(\omega)}$ in the first cavity via the first sound pickup sensor, and measuring a sound pressure $P_{21(\omega)}$ in the second cavity via the second sound pickup sensor; solving an equivalent acoustic capacitance $C_{a2}$ and an acoustic impedance $Z_{a2(\omega)}$ of the second cavity according to formula $$C_{a2} = \frac{V_2}{\rho C_0^2} \text{ and } Z_{a2(\omega)} = \frac{1}{\omega C_{a2}},$$

wherein $V_2$ is a volume of the second cavity, $\rho$ is air density, $C_0$ is the speed of sound, and $\omega$ is an angular frequency of the sound excitation source;

S3: solving formula $$Z_{ref(\omega)} = \frac{P_{11(\omega)} - P_{21(\omega)}}{P_{21(\omega)} \times \omega C_{a2}}$$

according to an equivalent acoustic circuit diagram when the sound absorption material is not placed in the device, and putting the equivalent acoustic capacitance $C_{a2}$ solved from step S2 into the formula to solve an acoustic impedance $Z_{ref(\omega)}$ of the slit channel;

S4: placing the sound absorption material to be tested in the second cavity, measuring a sound pressure $P_{12(\omega)}$ in the first cavity via the first sound pickup sensor, and measuring a sound pressure $P_{22(\omega)}$ in the second cavity via the second sound pickup sensor, solving formula $$Z_{L(\omega)} = \frac{P_{22(\omega)}}{\frac{P_{12(\omega)} - P_{22(\omega)}}{Z_{ref(\omega)}}}$$

according to an equivalent acoustic circuit diagram after the sound absorption material is placed in the device, putting the acoustic impedance $Z_{ref(\omega)}$ of the slit channel solved in step S3 into the formula to solve a uniform acoustic impedance $Z_{L(\omega)}$ after the sound absorption material is placed in the second cavity; and S5: solving formula $$Z_{L(\omega)} = \frac{\frac{1}{\omega C_{a2}} \times \frac{1}{\omega C_{dut}}}{\frac{1}{\omega C_{a2}} + \frac{1}{\omega C_{dut}}}$$

according to the equivalent acoustic circuit diagram after the sound absorption material is placed in the device, and solving an equivalent acoustic capacitance $C_{dut}$ of the sound absorption material; and then solving a capacity expansion amount $V_{dut}$ of the sound absorption material according to the formula $V_{dut} = \rho C_0^2 C_{dut}$, and thereby judging the impedance characteristic and expansion performance of the sound absorption material.

2. The method for testing impedance characteristic and expansion performance of a sound absorption material according to claim 1, wherein a sound pressure level needed by the test in step S1 is a sound pressure level of an actual working environment of the sound absorption material.

3. The method for testing impedance characteristic and expansion performance of a sound absorption material according to claim 1, wherein the sounding face of the sound excitation source flushes with a surface of an inner wall of the first cavity.

4. The method for testing impedance characteristic and expansion performance of a sound absorption material according to claim 1, wherein the sound excitation source is a speaker.

5. The method for testing impedance characteristic and expansion performance of a sound absorption material according to claim 1, wherein the two sound pickup sensor are both microphones.

6. The method for testing impedance characteristic and expansion performance of a sound absorption material according to claim 1, wherein the sound isolation material is one of metal, bakelite and acrylic.

* * * * *